(12) United States Patent
King et al.

(10) Patent No.: US 11,609,216 B2
(45) Date of Patent: Mar. 21, 2023

(54) ELECTRO-PNEUMATIC MODULE FOR ENHANCED GAS TITRATION/DILUTION PROCESSING

(71) Applicant: TELEDYNE INSTRUMENTS, INC., Thousand Oaks, CA (US)

(72) Inventors: Patrick M. King, San Diego, CA (US); Kirk W. Lovewell, El Cajon, CA (US)

(73) Assignee: TELEDYNE INSTRUMENTS, INC., Thousand Oaks, CA (US)

( * ) Notice: Subject to any disclaimer, the term of this patent is extended or adjusted under 35 U.S.C. 154(b) by 4 days.

(21) Appl. No.: 16/860,345

(22) Filed: Apr. 28, 2020

(65) Prior Publication Data

US 2021/0333255 A1 Oct. 28, 2021

(51) Int. Cl.
*G01N 33/00* (2006.01)
(52) U.S. Cl.
CPC ................. *G01N 33/0018* (2013.01)
(58) Field of Classification Search
CPC .................................................. G01N 33/0018
USPC .......................................................... 73/23.2
See application file for complete search history.

(56) References Cited

U.S. PATENT DOCUMENTS

| | | | | |
|---|---|---|---|---|
| 4,822,564 A | * | 4/1989 | Howard | G01N 21/766 250/361 C |
| 5,880,352 A | * | 3/1999 | Muench | G01N 33/0018 73/23.2 |
| 6,635,415 B1 | * | 10/2003 | Bollinger | G01N 33/0037 435/4 |
| 2004/0018630 A1 | * | 1/2004 | Birks | G01N 33/0037 436/116 |

FOREIGN PATENT DOCUMENTS

DE 102008038289 A1 * 2/2010 ........... G01N 1/2252

OTHER PUBLICATIONS

English translation of Muench (DE 102008038289) specification accessed from espacenet.com.*
EV Series Mouse Valves Technical Data Sheets, Clippard Instrument Laboratory, Inc., www.clippard.com, pp. 177-200 accessed Jan. 9, 2023 from https://www.clippard.com/downloads/PDF_Documents/Product%20Data%20Sheets/EV%20Series%20Mouse%20Valves.pdf.

* cited by examiner

*Primary Examiner* — David Z Huang
*Assistant Examiner* — Jean F Morello
(74) *Attorney, Agent, or Firm* — K&L Gates LLP (57) ABSTRACT

A gas mixing device for a NOx detector includes a 3/2 way gas valve having a diaphragm, a first inlet port, a second inlet port, and an exit port. A gas conduit connects the exit port to a gas mixing chamber. A controller controls the diaphragm to alternate between a first position and a second position. The first inlet port may receive a sample gas and the second inlet port may receive ozone gas. In the first position of the diaphragm, a bolus of sample gas enters the conduit, and in the second position of the diaphragm, a bolus of ozone enters the conduit. The alternating boluses of sample gas and ozone mix within the conduit and within the mixing chamber. A NOx detection instrument includes the gas mixing device, an ozone gas source, and an $NO_2$ sensor in fluid communication with the mixing chamber.

18 Claims, 5 Drawing Sheets

ELECTRO-PNEUMATIC MODULE FOR ENHANCED GAS TITRATION/DILUTION PROCESSING

BACKGROUND

Nitrogen oxides (NOx) are a family of poisonous, highly reactive gases. These gases form when fuel is burned at high temperatures. NOx pollution may be emitted by automobiles, trucks and various non-road vehicles (e.g., construction equipment, boats, etc.) as well as by industrial sources such as power plants, industrial boilers, cement kilns, and turbines. NOx often appears as a brownish gas. It is a strong oxidizing agent and plays a major role in the atmospheric reactions with volatile organic compounds (VOC) that produce ozone (smog) on hot summer days. NOx gases may react to form smog and acid rain as well as being central to the formation of fine particles (PM) and ground level ozone, both of which are associated with adverse health effects. NOx is known to have an adverse impact on respiratory conditions causing inflammation of the airways at elevated levels. Long term exposure can decrease lung function, increase the risk of respiratory conditions and increases the response to allergens. Elevated levels of NOx can also have a negative effect on vegetation, including leaf damage and reduced growth. The Clean Air Act Amendments of 1990 require major stationary sources of NOx to reduce and control the emission of such gasses.

The U.S. Environmental Protection Agency (EPA) has promulgated desired standards for reducing the amount of NOx production by heavy-duty trucks as well as stationary emission sites, typically referred to as source emissions. In conjunction with standards to address source emissions the EPA has also promulgated standards to regulate ambient levels of NOx under the Clean Air Act. The Clean Air Act, which was last amended in 1990, requires EPA to set National Ambient Air Quality Standards (40 CFR part 50) for pollutants considered harmful to public health and the environment. The Clean Air Act identifies two types of national ambient air quality standards. Primary standards provide public health protection, including protecting the health of "sensitive" populations such as asthmatics, children, and the elderly. Secondary standards provide public welfare protection, including protection against decreased visibility and damage to animals, crops, vegetation, and buildings. In order to certify that a vehicle or site meets the required standards NOx testing instruments must be devised with sufficient sensitivity to measure NOx concentrations below the required minimum standard.

NOx generally comprises a combination of nitric oxide (NO) and nitrogen dioxide ($NO_2$). Since the standards are directed to the total amount of nitrogen oxide compounds, a testing instrument may determine the amount of NO and $NO_2$ separately, or a combination thereof. In some testing instruments, NOx is completely converted to NO by catalytic means. Such instruments may then measure the amount of NO (from native NO or catalyzed $NO_2$) through any suitable detection method, for example chemiluminescence. Such detectors may be expensive and require significant amounts of maintenance. It is therefore useful to develop a test instrument for NOx that is cost effective and requires minimum maintenance for continued operations.

SUMMARY

In one aspect, a gas mixing device for a gas analyzer may include an electronically actuated 3/2 way gas valve having a diaphragm, a first inlet port, a second inlet port, and an exit port. A conduit may be in fluid communication with the exit port at a first end of the conduit and a mixing chamber may be in fluid communication with a second end of the conduit. A controller may be configured to control a position of the diaphragm within the electronically actuated 3/2 way gas valve, and the second inlet port may be configured to receive ozone gas from an ozone gas source.

In another aspect, a NOx detection instrument may include a gas mixing device having an electronically actuated 3/2 way gas valve having a diaphragm, a first inlet port, a second inlet port, and an exit port. A conduit may be in fluid communication with the exit port at a first end of the conduit and a mixing chamber may be in fluid communication with a second end of the conduit. A controller may be configured to control a position of the diaphragm within the electronically actuated 3/2 way gas valve. The NOx detection instrument may include an ozone gas source in fluid communication with the second inlet port of the 3/2 way gas valve. Additionally, an $NO_2$ sensor may be in fluid communication with the mixing chamber.

In yet another aspect, a method of measuring a concentration of NOx in a sample gas, may include controlling, by a controller, a diaphragm within an electrically actuated 3/2 way gas valve to assume a first configuration, controlling, by the controller, the diaphragm within the electrically actuated 3/2 way gas valve to assume a second configuration, causing, by the controller, the diaphragm to alternately assume the first configuration and the second configuration within the electrically actuated 3/2 way gas valve, directing a bolus of a sample gas to flow from a first input port of the 3/2 way gas valve into a conduit in fluid communication with an exit port of the 3/2 way gas valve when the diaphragm assumes the first configuration, directing a bolus of ozone to flow from a second input port of the 3/2 way gas valve into the conduit when the diaphragm assumes the second configuration, directing the bolus of sample gas in the conduit and the bolus of ozone in the conduit to enter a mixing chamber, mixing, within the mixing chamber, the ozone and sample gas to form a gas mixture, and measuring, by a $NO_2$ detector, a concentration of $NO_2$ in the gas mixture.

FIGURES

Various features of the aspects described herein are set forth with particularity in the appended claims. The various aspects, however, both as to organization and methods of operation, together with advantages thereof, may be understood in accordance with the following description taken in conjunction with the accompanying drawings as follows:

DESCRIPTION

The U.S. Environmental Protection Agency (EPA) has promulgated desired standards for reducing the amount of NOx in ambient environments, close to urban populations, as well as NOx production by heavy-duty trucks and stationary emission sites. In one example the 1 hour averaged $NO_2$ ambient criteria pollutant level is restricted to 100 ppb. In order to certify that a vehicle, site, or ambient environment meets the required standards, NOx testing instruments must be devised with sufficient sensitivity to measure NOx values to concentrations below the required minimum standards.

NOx generally comprises a combination of nitric oxide (NO) and nitrogen dioxide ($NO_2$). Since the standards are directed to the total amount of nitrogen oxide compounds, a testing instrument may determine the amount of NO and $NO_2$ separately, or a combination thereof. In some testing instruments, NOx is completely converted to NO by catalytic means. Such instruments may then measure the amount of NO (from native NO or catalyzed $NO_2$) through any suitable detection method, for example chemiluminescence. Such detectors, however, are expensive and require significant maintenance. It is therefore useful to develop a test instrument for NOx that is cost effective and requires minimum maintenance for continued operations.

Figure 1:
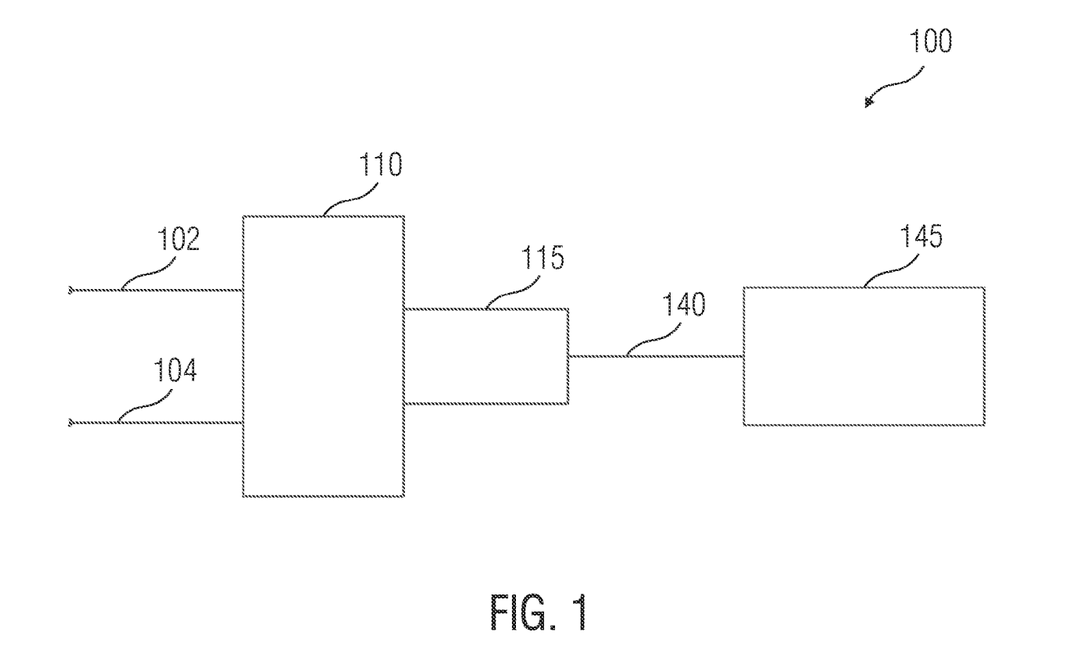
FIG. 1 depicts a diagram of a general aspect of a NOx testing device, according to an aspect of the present disclosure.

As an alternative to the chemiluminescence system disclosed above, a NOx testing instrument may convert the NO component of NOx to $NO_2$. The total concentration of $NO_2$ may then be measured in any suitable manner, such as spectrophotometrically. Instead of relying on a catalytic conversion of the $NO_2$ to NO, a system may generate $NO_2$ from the combination of gaseous NO with ozone ($O_3$). The mixture may spontaneous convert the NO and $O_3$ into $NO_2$ and $O_2$. FIG. 1 schematically illustrates such a test instrument 100. The test instrument 100 is composed of a valving component 110, a mixing chamber 115, a mixing chamber conduit 140, and a sensor unit 145. A gaseous stream of ozone 104 and a stream of the gas under test 102 may enter the valving component 110. The gasses may be directed to the mixing chamber 115 where the ozone and gas under test combine and react. The gas mixture output of the mixing chamber 115 may then be directed by the mixing chamber conduit 140 to the sensor unit 145 where the concentration of $NO_2$ may be measured. It may be recognized that the gas under test may include any appropriate gas for testing. For example, the test instrument 100 may require calibration. The gas under test may include gasses with known concentrations of NO or $NO_2$. Zero gas, for example, which lacks any NOx components, may be used to calibrate a zero measurement for the sensor unit 145. Span gas, having known non-zero concentrations of NO, $NO_2$, or a combination therefore, may be used to calibrate the response of the sensor unit 145. After calibration, the test instrument 100 may then receive a sample gas from an environmental source, having an unknown concentration of NOx components, as the gas under test.

It may be recognized that it is critical that all or essentially all of the NO in the sample be converted to $NO_2$ for the proper determination of the NOx concentration in the sample. Since only the $NO_2$ concentration is measured by the sensor unit 145, unreacted NO will not be measured and consequently the total NOx concentration in the sample may be under-determined. As disclosed above, mixing NO with ozone spontaneously results in $NO_2$ and $O_2$. Therefore, complete mixing of the sample gas with ozone is required.

Figure 2:
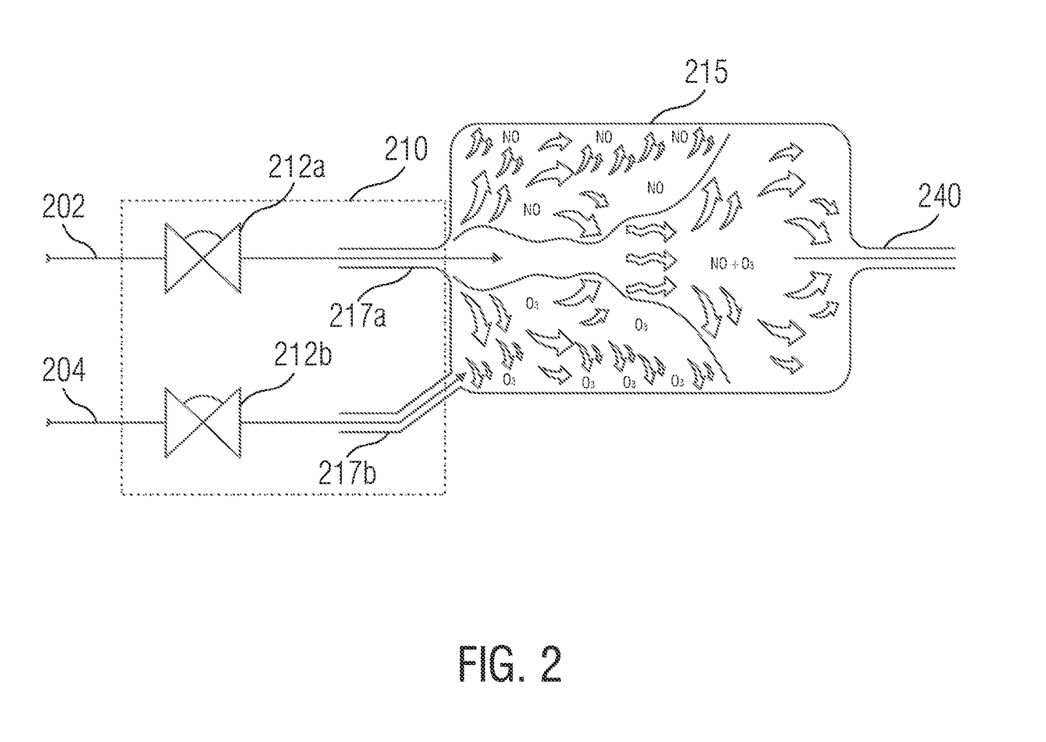
FIG. 2 depicts a diagram of one aspect of a mixing system of a NOx testing device, according to an aspect of the present disclosure.

FIG. 2 depicts an apparatus and method of mixing NO with ozone as may be found in some current NOx testing instruments. A stream of the sample gas 202 and a stream of ozone 204 are directed separately into the valving component 210. Within the valving component 210 are two independent 2/2 way valves 212a and 212b which separately control an amount of the sample gas and an amount of ozone to be passed to the mixing chamber 215. Specifically, 2/2 way valve 212a controls an amount of sample gas and 2/2 way valve 212b controls an amount of ozone to enter the mixing chamber 215. The portion of sample gas controlled by 2/2 way valve 212a enters the mixing chamber 215 via a sample gas conduit 217a. Similarly, the portion of ozone controlled by 2/2 way valve 212b enters the mixing chamber 215 via an ozone conduit 217b. As depicted in FIG. 2, each gas enters the mixing chamber 215 separately.

At a proximal end of the mixing chamber 215, (that is, the end closest to the valves) the two gasses may experience laminar or quasi-laminar flow resulting in minimal mixing. As the reaction rate is dependent on the quality of gas mixing, the laminar or quasi-laminar flow may result in minimal gas mixing thereby producing a minimal gas reaction rate. Mixing may occur through gaseous diffusion throughout more distal portions of the body of the mixing chamber 215. Given the reactive nature of the two gases, it may be recognized that improved physical mixing of the gas species results in improved reaction of the two gases. It may be understood that the portion of the volume of the mixing chamber 215 in which the sample gas and ozone react (reaction volume) also depends on the relative velocities of the two gases. Without being bound by theory, slower gas velocities may result in mixing at a more proximal end of the mixing chamber 215, resulting in a larger reaction volume, while faster gas velocities may result in mixing at more distal end of the mixing chamber 215, resulting in a smaller reaction volume. There is therefore a trade-off regarding the rate of gas flow and ultimately NOx detection. A slow gas flow rate may result in a larger reaction volume in the mixing chamber 215 and greater conversion of NO to $NO_2$. However, the slow gas flow rate may increase the time required to detect the NOx concentration and reduce the temporal resolution of the gas analysis. Alternatively, a fast gas flow rate may result in a decrease in the time required to detect the NOx concentration and increase the temporal resolution of the gas analysis. However, the fast gas flow rate may result in a smaller reaction volume in the mixing chamber 215 resulting in a decreased conversion of NO to $NO_2$. In some alternative examples, gas flowing at a sufficiently high rate, with or without modified flow entry conditions, may result in turbulent flow of the sample gas and/or ozone, and may lead to improved gas reaction times.

The output gas mixture from the mixing chamber 215, may be directed from the mixing chamber conduit 240 to the sensor unit (not shown) where the concentration of $NO_2$ may be measured.

There may be increased process control overhead in the system depicted in FIG. 2 due to the use of two separate 2/2 way valves 212a,b. In some aspects, each of the 2/2 way valves 212a,b may be an on/off valve. In some alternative aspects, each of the 2/2 way valves 212a,b may be a proportional valve. Each valve may be separately controlled. It may be recognized that the amount of each gas must be precisely controlled to maintain the optimal stoichiometry of gas concentration. As indicated in the gas phase titration equation below $$NO+O_3 \rightarrow NO_2+O_2$$

a slight molar excess of ozone over NO may be required to assure complete conversion of NO to $NO_2$ in the sample gas when properly mixed. This would require fine control of the relative operations of the two valves to assure proper rationing of the sample gas and ozone. This may be especially important if the valves are 2/2 way on/off valves. Thus, the outputs of both valves should be calibrated to assure that their gas flow parameters are properly matched. Commonly, two separated flow controllers are located before the valves to maintain proper rationing. Further, complete or partial failure of either valve would require extensive troubleshooting to properly assess the type of failure and necessary repair strategy.

Therefore, it may be recognized that a mixing design as depicted in FIG. 2 may not provide a cost effective or efficient solution for a NOx testing instrument.

Figure 3:
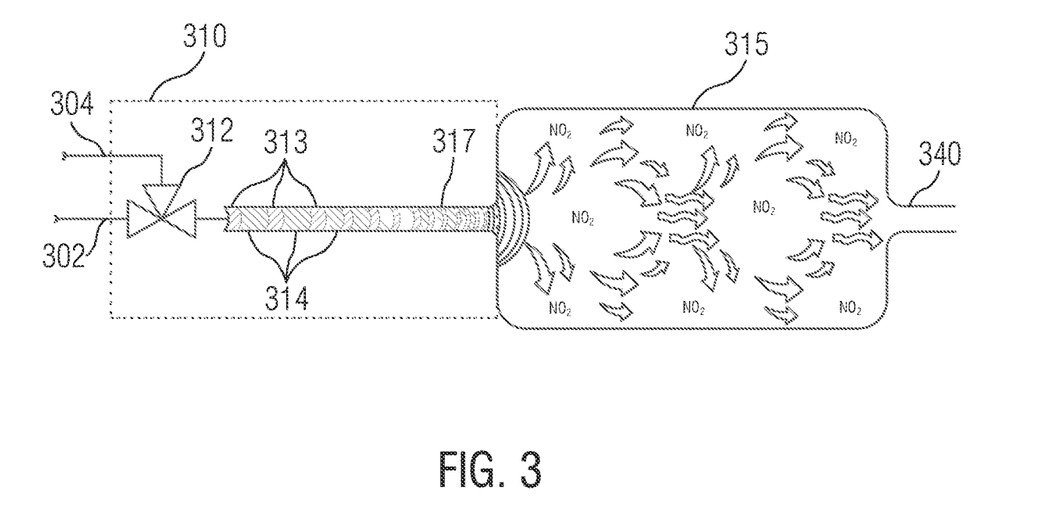
FIG. 3 depicts a diagram of a second aspect of a mixing system of a NOx testing device, according to an aspect of the present disclosure.

FIG. 3 depicts an alternative embodiment of an apparatus and method of mixing NO with ozone. A stream of the sample gas 302 and a stream of ozone 304 are directed separately into the valving component 310. Within the valving component 310 is a single valve 312 which alternately directs the sample gas and the ozone into a single conduit 317. In some aspects, valve 312 may be a 3/2 way valve. In a first phase of operation, the valve 312 may permit a bolus of the sample gas 314 from the sample gas stream 302 to enter conduit 317. In a second phase of operation, the valve 312 may permit a bolus of ozone 313 from the ozone stream 304 to enter conduit 317. As a result, there may be boluses of ozone 313 alternating with boluses of sample gas 314 that traverse the conduit 317.

The phases of operation of the valve 312 may be based on a timing parameter that permit the valve 312 to switch the gas streams entering the conduit 317. In some non-limiting examples, the valve 312 may have a minimum switching response time of about 10 msec. to about 50 msec. The amount of each type of gas entering the conduit 317 may be determined by an amount of time the valve 312 is in a specified phase of operation. Depending on the mode of operation, the valve 312 may switch phase for about 10 msec. to about 100 msec. In other modes of operation, the valve 312 may switch phase for about 10 msec. to about 1000 msec. The timing of the valve 312 may permit a first gas to enter the conduit 317 for a first length of time and permit a second gas to enter the conduit 317 for a second length of time. The first length of time may be the same as the second length of time or may differ from the second length of time. The valve 312 may be sequentially actuated, thereby alternatively sourcing a first gas for a first period of time and a second gas for a second period of time. Sequential actuation may maintain the same lengths of time for the sourcing of each gas. Alternatively, sequential actuation may require changes in the lengths of time for the sourcing of any one or both gases. As one non-limiting example, the valve 312 may switch phase to permit ozone to enter the conduit 317 for about 20 msec. In another non-limiting example, the valve 312 may switch phase to permit the sample gas to enter the conduit 317 for about 600 msec. In one aspect, an amount of time the valve 312 permits a first gas to enter the conduit 317 may differ from an amount of time the valve 312 permits a second gas to enter the conduit 317. In an alternative aspect, an amount of time the valve 312 permits a first gas to enter the conduit 317 may be the same as an amount of time the valve 312 permits a second gas to enter the conduit 317.

It may be recognized that the volume or amount of gas in a gas bolus may be determined based on the amount of time the valve 312 is set in one of the two phases of operation. In some aspects, the timing for each phase of operation of the valve 312 may be selected by a controller in order to optimize the mixing of the two gases. The boluses of ozone 313 alternating with boluses of sample gas 314 may traverse the conduit 317 and enter the mixing chamber 315, i.e. the reaction chamber, wherein the gasses may mix further to produce $NO_2$. It may be understood that the valve 312 should have a sufficiently fast response time to rapidly switch between the gas streams. If the switching time is too slow, a first bolus of gas in the conduit 317 may diffuse away from a subsequent bolus of gas, thereby reducing the gas concentrations at the interface between the two boluses. Such a reduced gas concentration may reduce the amount of gases reacting at the interface.

In some examples, the gas mixing system as depicted in FIG. 3 may also include one or more controllers. The controllers may include one or more processing units and one or more memory units configured to store instructions and/or data for use by the processing units. The one or more processing units may include one or more micro-processors, FPGAs, or any other processing device. In some examples, the memory units may include static memory units such as PROMs or EPROMS and/or dynamic memory units. The dynamic memory units may temporarily store data for use by the one or more processing units. The static memory units may be configured to store instructions that, when executed by the one or more processing units, may cause the one or more processing units to carry out one or more logical operations or calculations.

The controller may also include one or more interfaces to receive data from one or more sensors (for example a spectrophotometric sensor for sensing an amount of $NO_2$). The controller may also include one or more interfaces to send data or control signals to one or more components to actuate the one or more components (for example, control signals to electronics capable of actuating a 3/2 way valve). For example, the static memory units may include instructions that permit the one or more processing units to calculate $NO_2$ concentration data from electronic data received from a sensor. Additional instructions may cause the one or more processing units to determine an optimized ratio of ozone to sample gas in the mixing chamber based on the data received from the $NO_2$ sensor. Such an optimized ratio may result in maximizing the conversion of NO in the sample gas to $NO_2$. The one or more processing units may then actuate the 3/2 way valve to change the amount of time the valve spends in the first phase of operation (permitting ozone to flow into the conduit 317) relative to the amount of time the valve spends in the second phase of operation (permitting sample gas to flow into the conduit 317). In this manner, the instructions may cause the one or more processing units to adjust the volumes of the alternating ozone bolus 313 and sample gas bolus 314 in the conduit 317.

As noted above, ozone and NO spontaneously react to form $O_2$ and $NO_2$ on mixing. Within the conduit 317, a bolus of ozone 313 may contact neighboring boluses of the sample gas 314 on either side. As a result, some mixing may occur at the interfaces of the ozone bolus 313 and neighboring sample gas boluses 314, resulting in some initial conversion of NO in the sample gas bolus 314 to $NO_2$. In some aspects, depending on the type of flow of the gasses through the conduit 317 (laminar or turbulent) and the conduit 317 geometry, the boluses 313, 314 may be sufficiently mixed together before entering into the mixing chamber 315. Without being bound by theory, premixing of the boluses 313 and 314 together may increase the NO oxidation by ozone within the conduit 317 even further. Additional mixing of ozone and sample gas may then occur within the mixing chamber 315. The output of the mixing chamber 315, may be directed via the mixing chamber conduit 340 to the sensor unit (not shown) where the concentration of $NO_2$ is measured.

It may thus be recognized that mixing of the gasses in the system depicted in FIG. 3 may be more complete compared to the gas mixing in the system depicted in FIG. 2. One can further recognize that no trade-offs regarding gas flow, as found in the aspect depicted in FIG. 2, may be required in the system depicted in FIG. 3. Additional improvements found in the aspect depicted in FIG. 3 further include a simpler and less expensive design than that depicted in FIG. 2. The aspect of FIG. 3 relies only on a single 3/2 way valve 312, which saves the cost of using two valves (212a,b in FIG. 2). Further, gas control is simpler since it depends only on the timing of the valve motion between the first phase and the second phase of operation and not require the use of multiple external flow controllers.

Figure 4:
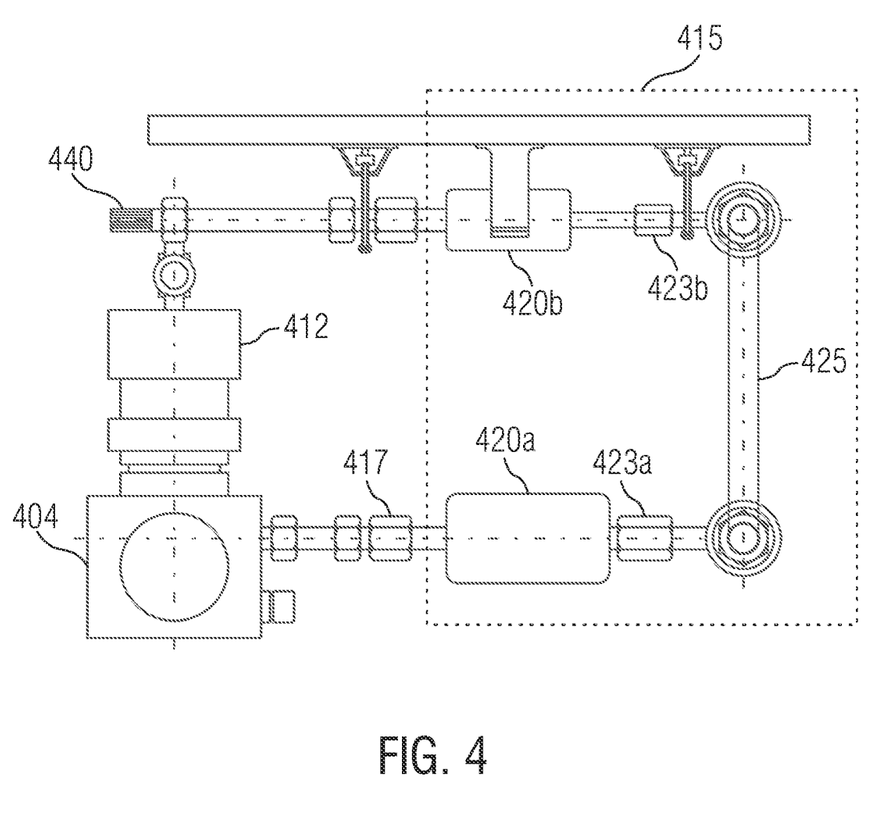
FIG. 4 illustrates a portion of a mixing system of a NOx testing device as depicted in FIG. 3, according to an aspect of the present disclosure.

FIG. 4 illustrates a realization of the enhanced mixing system depicted in FIG. 3. FIG. 4 illustrates the single 3/2 way valve 412 attached to a source of ozone 404. The source of the sample gas is not illustrated in FIG. 4. In some aspects, the ambient air surrounding the components depicted in FIG. 4 may be serve as the source of the sample gas. Conduit 417 directs the effluent from the 3/2 way valve 412 to the mixing chamber 415. In one aspect, mixing chamber 415 may be composed of a single section. In some alternative aspects, mixing chamber 415 may be composed of multiple sections. As depicted in FIG. 4, mixing chamber 415 may be composed of the following components. A first disposable filter unit (DFU) 420a may receive the gas mixture from the conduit 417. The gas mixture in the first DFU 420a may be directed to a transfer tube 425 via a first elbow fixture 423a. The gas in the transfer tube 425 may then be directed to a second DFU 420b via a second elbow fixture 423b. The output of the mixing chamber 415, may be directed by the mixing chamber conduit 440 to the sensor unit (not shown) where the concentration of $NO_2$ may be measured. In some aspects, the first and second DFU (420a, b) may include non-reactive components or fillings. Non-limiting examples of such components or fillings may include any one or more of microporous borosilicate glass, beads, interior fins, or other structures designed to improve mixing therein. Although FIG. 4 illustrates a mixing chamber 415 composed of multiple parts, it should be understood that such parts are non-limiting, and that the mixing chamber 415 may be composed of any one or more components configured to assure the mixing of the ozone and sample gas therein before being measured by the sensor unit.

Figure 5:
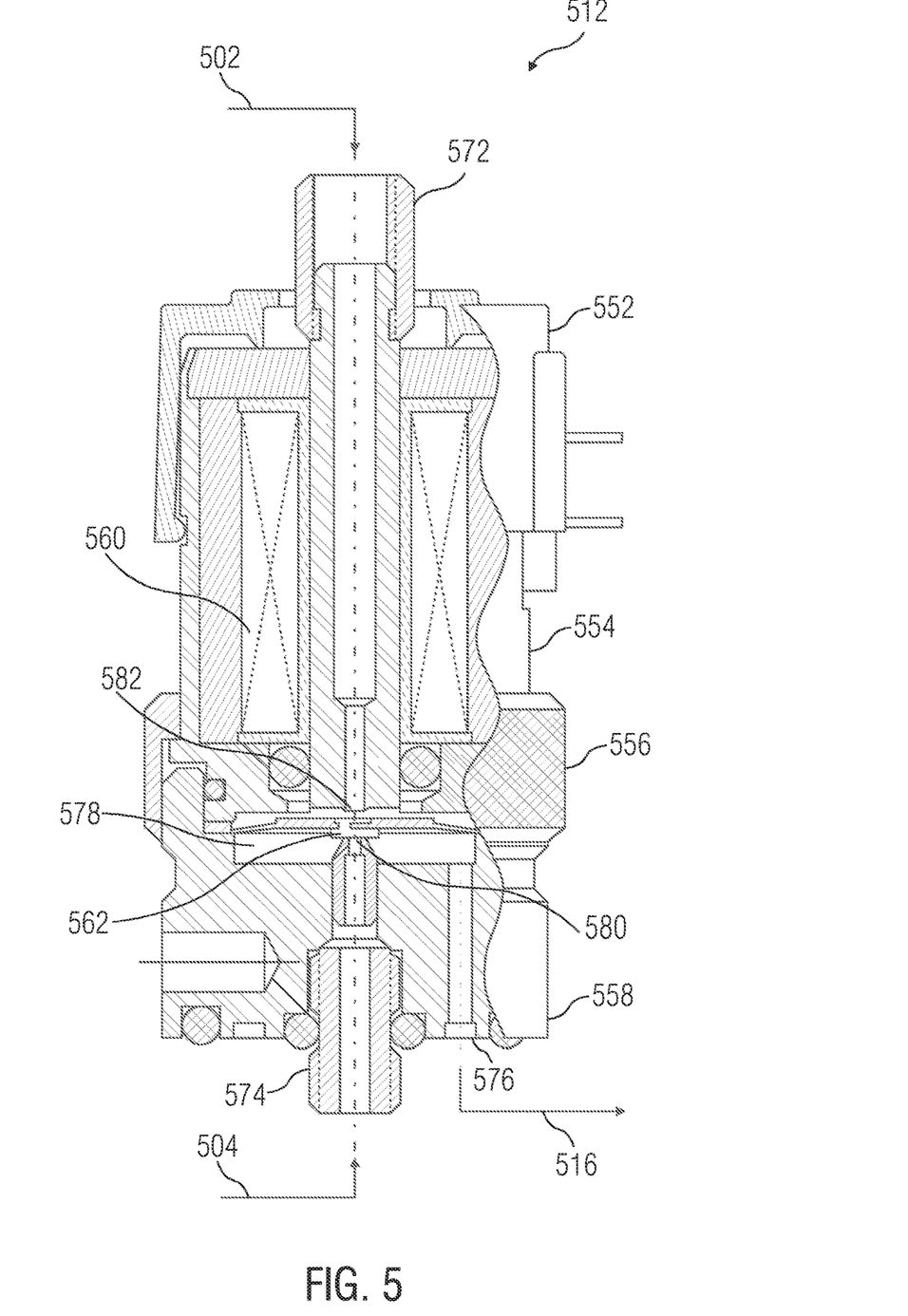
FIG. 5 depicts a longitudinal sectional view of a 3/2 way valve which may be used in the mixing system depicted in FIG. 3, according to an aspect of the present disclosure.

FIG. 5 illustrates a longitudinal sectional view of an electronically actuated 3/2 way valve 512, similar to 3/2 way valve 412 depicted in FIG. 4. It may be recognized that electronically actuated valve 512 is only one example of a 3/2 way valve, and is not considered limiting in terms of its construction or operation. A stream of sample gas 502 may enter into the valve 512 through a first inlet port 572 and a stream of ozone 504 may enter into the valve 512 through a second inlet port 574. Valve 512 may include a cap 552 secured to an upper body portion 554. Adjusting ring 556 may secure the upper body portion 554 to a lower body portion 556. Within the upper body portion 554 may be a solenoid coil 560 configured to actuate a diaphragm 562. The solenoid coil 560 may receive current from any appropriately controlled power supply. The diaphragm 562 may be positioned by a magnetic field generated by the solenoid coil 560 to occlude either an interior sample gas port 582 or an interior ozone port 580. In some examples, the electronically actuated 3/2 way valve 512 may have the diaphragm 562 in a normally open/normally closed configuration with respect to the first inlet port 572 and the second inlet port 574, respectively. In some alternative examples, the electronically actuated 3/2 way valve 512 may have the diaphragm 562 in a normally closed/normally open configuration with respect to the first inlet port 572 and the second inlet port 574, respectively. An internal exit volume 578 may receive either the sample gas or the ozone depending on the position of the diaphragm 562. The gas within the internal exit volume 578 may then exit the valve 512 through an exit bore 576 to form an effluent stream 516. The effluent stream 516 may then be directed to the mixing chamber (not shown) for additional gas mixing.

In some examples, the internal exit volume 578 may be formed by a combination of a volume formed by an interior portion at the base of the upper body portion 554, a section surrounding the diaphragm 562, and an interior portion at the top of the lower body portion 558. The internal exit volume 578 may also be in fluid connection with a volume formed by the exit bore 576. In one example, the combination of the volume of the exit bore 576 plus the internal exit volume 578 may be about 0.41 $cm^3$. In a further example, the total volume of the mixing chamber 415 as depicted in FIG. 4 may be about 15.5 $cm^3$. The total mixing volume including that of the valve and the mixing chamber may be about 15.9 $cm^3$. It may be recognized that an input gas flow at about 1000 $cm^3$/min. through such a system may result in a total residence time in the system for gas mixing (thus the total gas reaction time) that is less than one second (about 0.94 sec). Again, it is recognized that such values are merely examples to indicate the potential capability of such a system as depicted in FIG. 4.

As a further example, the 3/2 way valve 512 may be characterized by a variety of operational parameters. The values listed herein may be taken as mere examples and are not intended to be limiting. Thus, in one example, the valve may be essentially cylindrical having an overall height of about 1.3 inches (33.0 mm) and a diameter of about 0.72 inches (18.3 mm). The valve solenoid may operate at any useful DC voltage, for example at 12 VDC or 24 VDC with a power consumption of about 1 W. The valve may operate with external gas pressures between vacuum and about 105 psig (724 kPa). The diaphragm may have a response time at nominal voltage of about 15 msec. Using a gas flow of about 1000 $cm^3$/min., at a 15 msec. response time, a gas bolus of about 0.5 $cm^3$ may be generated, indicating that very small alternating gas boluses may be generated to improve NO and ozone mixing within the apparatus.

As disclosed above, a 3/2 way gas valve may be programmed to alternate the introduction of a sample gas and ozone into a mixing or reaction chamber to allow the ozone to react with any NO present. The resulting $NO_2$ may be measured by a detector to determine the total NOx concentration in the sample. It may be recognized that a NOx detector may require calibration. Calibration may include determining a zero response of the detector when no NO or $NO_2$ is present in a sample gas. The zero response of the detector may be determined using zero gas as the sample. Additionally, calibration may include determining a response of the detector when a sample having a known concentration of NO and/or $NO_2$ is present. In some calibration examples, the sample gas may be a span gas having a known concentration of NO and/or $NO_2$. In some aspects, the span gas may have a concentration of NO and/or $NO_2$ that may result in the detector having a maximum response.

The gas mixing system above is disclosed in the context of measuring an $NO_2$ concentration resulting from the gas titration of a sample containing some amount of NO with ozone. It may be recognized that the gas mixing system may equally be used in the context of measuring the product from mixing any two highly reactive gases. As indicated above, the reaction of two reactive gases is dependent on the thoroughness of mixing. Further, the time actuation of the 3/2 way valve is ideal to adjust the stoichiometry of the mixing gases regardless of the types of gases being mixed.

The 3/2 way valve and mixing system disclosed above can equally be used for precise gas mixing applications. Thus, for calibration purposes, it may be useful to have a sample of a gas having a known NO concentration that lies between that of a (concentrated) span gas and a zero gas. The 3/2 way valve may be actuated in an alternating manner to supply a known amount of the span gas followed by a known amount of the zero gas. As an example, the valve may alternatingly open the output port to a span gas for 10 msec. followed by opening the output port to a zero gas for 1000 msec. In that manner, the resulting gas will have a defined NO concentration of $1/10^{th}$ the concentration of the span gas. It may be recognized that different outflow gas concentrations may be created based on the relative timing of the valve position. Alternatively, the sample gas may have such a high concentration of NOx components that the NOx concentration may lie outside the dynamic range of the sensor. In this case, the sample may have to be diluted to a known amount in order to properly measure the amount of NOx components in the sample. In such a case, the sample may be diluted using a zero gas by a known amount before being reacted with the ozone in the measuring instrument in a similar manner.

Similarly, the gas mixing system may be used to enhance the concentration of a component gas in a sample having a low concentration. In one aspect, a sample gas may have a low NO concentration that may be barely detectable by the sensor. In order to assure that the sensor is operating properly, it may be useful to deliberately introduce some amount of NO (by mixing a known amount of span gas) to be certain that the system operates properly. In this example, the output port of the 3/2 way valve may alternatingly receive an amount of the sample gas along with an amount of the span gas, thereby deliberately enhancing the NO content. In this manner, low measured concentrations of NO gas in the sample can be verified by the admixture of a known amount of NO.

Reference throughout the specification to "various embodiments," "some embodiments," "one embodiment," "an embodiment", "one aspect," "an aspect" or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures or characteristics may be combined in any suitable manner in one or more aspects. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

While various details have been set forth in the foregoing description, it will be appreciated that the various aspects of the present disclosure may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

Some or all of the embodiments described herein may generally comprise technologies for various aspects, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. Those skilled in the art will recognize, however, that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A gas reaction device for a gas analyzer, the reaction device comprising:
   an electronically actuated 3/2 way gas valve having a diaphragm, a first inlet port, a second inlet port, and an exit port;
   a conduit directly connected to and in fluid communication with the exit port at a first end of the conduit;
   a reaction chamber directly connected to and in fluid communication with a second end of the conduit, wherein the reaction chamber comprises a first filter unit directly connected to the conduit, a transfer tube directly connected to the first filter unit at a first end of the transfer tube, and a second filter unit directly connected to the transfer tube at a second end of the transfer tube; and
   a controller configured to control a position of the diaphragm within the electronically actuated 3/2 way gas valve,
   wherein the first inlet port is configured to receive a sample gas from a sample gas source,
   wherein the second inlet port is configured to receive ozone gas from an ozone gas source, and
   wherein the reaction chamber is configured to mix the ozone gas with the sample gas to chemically react the sample gas with the ozone gas.

2. The gas reaction device of claim 1, wherein the controller is configured to adjust a period of time during which the diaphragm is in a first configuration within the 3/2 way gas valve.

3. The gas reaction device of claim 2, wherein the period of time during which the diaphragm is in the first configuration is between 10 msec. and 100 msec.

4. The gas reaction device of claim 1, wherein the controller is configured to adjust a period of time during which the diaphragm is in a second configuration within the 3/2 way gas valve.

5. The gas reaction device of claim 4, wherein the period of time during which the diaphragm is in the second configuration is between 10 msec. and 1000 msec.

6. The gas reaction device of claim 1, wherein the sample gas comprises a specified composition comprising a known concentration of NO, $NO_2$, or a combination thereof.

7. The gas reaction device of claim 1, wherein the controller is configured to control the position of the diaphragm to alternately permit the ozone gas and the sample gas to enter the conduit.

8. A NOx detection instrument comprising:
   a gas reaction device comprising:
      an electronically actuated 3/2 way gas valve having a diaphragm, a first inlet port, a second inlet port, and an exit port, wherein the first inlet port is configured to receive a sample gas from a sample gas source;
      a conduit directly connected to and in fluid communication with the exit port at a first end of the conduit;
      a reaction chamber directly connected to and in fluid communication with a second end of the conduit, wherein the reaction chamber comprises a disposable filter unit directly connected to the conduit, a transfer tube directly connected to the first filter unit at a first end of the transfer tube, and a second filter unit directly connected to the transfer tube at a second end of the transfer tube; and a controller configured to control a position of the diaphragm within the electronically actuated 3/2 way gas valve;

an ozone gas source in fluid communication with the second inlet port of the 3/2 way gas valve, wherein the reaction chamber is configured to mix the ozone gas with the sample gas to chemically react the sample gas with the ozone gas; and an $NO_2$ sensor in fluid communication with the mixing chamber.

9. The NOx detection instrument of claim 8, wherein the controller is configured to adjust a period of time during which the diaphragm is in a first configuration within the 3/2 way gas valve.

10. The NOx detection instrument of claim 9, wherein the period of time during which the diaphragm is in the first configuration is between 10 msec. and 100 msec.

11. The NOx detection instrument of claim 8, wherein the controller is configured to adjust a period of time during which the diaphragm is in a second configuration within the 3/2 way gas valve.

12. The NOx detection instrument of claim 11, wherein the period of time during which the diaphragm is in the second configuration is between 10 msec. and 1000 msec.

13. The NOx detection instrument of claim 8, wherein the controller is configured to adjust a period of time during which the diaphragm is in a first configuration or a period of time during which the diaphragm is in a second configuration based at least in part on a $NO_2$ concentration detected by the $NO_2$ sensor.

14. The NOx detection instrument of claim 8, wherein the sample gas comprises a specified composition comprising a known concentration of NO, $NO_2$, or a combination thereof.

15. The NOx detection instrument of claim 8, wherein the controller is configured to control the position of the diaphragm to alternately permit the ozone gas and the sample gas to enter the conduit.

16. A method of measuring a concentration of NOx in a sample gas, the method comprising:

controlling, by a controller, a diaphragm within an electrically actuated 3/2 way gas valve to assume a first configuration;

controlling, by the controller, the diaphragm within the electrically actuated 3/2 way gas valve to assume a second configuration;

causing, by the controller, the diaphragm to alternately assume the first configuration and the second configuration within the electrically actuated 3/2 way gas valve;

directing a bolus of a sample gas to flow from a first input port of the 3/2 way gas valve into a first end of a conduit directly connected to and in fluid communication with an exit port of the 3/2 way gas valve when the diaphragm assumes the first configuration for 10 msec. to 100 msec.;

directing a bolus of ozone to flow from a second input port of the 3/2 way gas valve into the first end of the conduit when the diaphragm assumes the second configuration for 10 msec. to 1000 msec.;

reacting, in the conduit, a portion of the bolus of the sample gas and a portion of the bolus of the ozone at a gaseous interface therebetween;

directing the bolus of sample gas in the conduit and the bolus of ozone in the conduit to enter a reaction chamber, wherein a second end of the conduit is directly connect to and in fluid communication with the reaction chamber;

further reacting, within the reaction chamber, of the ozone and sample gas to form a gas mixture resulting from a chemical reaction between the sample gas and the ozone; and measuring, by a $NO_2$ detector, a concentration of $NO_2$ in the gas mixture.

17. The method of claim 16, wherein directing a bolus of a sample gas comprises directing a bolus of a sample gas comprising a known amount of NO, $NO_2$, or combination thereof.

18. The method of claim 17, further comprising:
calibrating the $NO_2$ detector using the sample gas.

* * * * *